United States Patent [19]
Koulik et al.

[11] Patent Number: 6,143,354
[45] Date of Patent: Nov. 7, 2000

[54] ONE-STEP METHOD FOR ATTACHMENT OF BIOMOLECULES TO SUBSTRATE SURFACES

[75] Inventors: Edouard Koulik, ET Maastricht; Michel Verhoeven, BD Maastricht, both of Netherlands; Patrick Cahalan; Linda Cahalan, both of Windham, N.H.

[73] Assignee: Medtronic Inc., Minneapolis, Minn.

[21] Appl. No.: 09/245,840

[22] Filed: Feb. 8, 1999

[51] Int. Cl.$^7$ .............................. A61L 15/00; A61L 27/00; H05H 1/00

[52] U.S. Cl. ...................... 427/2.24; 427/2.25; 427/2.27; 427/2.28; 427/2.3; 427/2.31; 427/537

[58] Field of Search ................................ 427/2.24, 2.25, 427/2.27, 2.28, 2.3, 2.31, 533, 535, 537

[56] References Cited

U.S. PATENT DOCUMENTS

| | | | |
|---|---|---|---|
| 5,229,172 | 7/1993 | Cahalan et al. | 427/536 |
| 5,356,433 | 10/1994 | Rowland et al. | 623/11 |
| 5,607,475 | 3/1997 | Cahalan et al. | 623/11 |
| 5,945,457 | 8/1999 | Plate et al. | 514/772.1 |

FOREIGN PATENT DOCUMENTS

WO 93/14127  7/1993  WIPO .

OTHER PUBLICATIONS

A. Nagaty, F., et al.; Graft Polymerization of Vinyl Monomers onto Starch by use of Tetravalent Cerium; European Polymer Journal, vol. 16, pp. 343–346, Jul. 17, 1979.

Lindhout et al., *J. Biomed. Mater. Res.*, 29, 1255–1256.

Lindhout et al., *J. Mater. Sci. Mater. Med.*, 6, 367 (1995).

Nagaty et al., "Graft Polymerization of Vinyl Monomers onto Starch by use of Tetravalent Cerium," *European Polymer Journal,* 16, 343–346 (1980).

Onishi, "Effects of dextran molecular weight on graft copolymerization of dextran–methyl methacrylate," *Polymer,* 21, 819–824 (1980).

Park et al., "Heparin immobilization onto segmented polyurethaneurea surfaces—effect of hydrophilic spacers," *Journal of Biomedical Materials Research,* 22, 977–992 (1988).

*Primary Examiner*—Shrive Beck
*Assistant Examiner*—Jennifer Kolb
*Attorney, Agent, or Firm*—Thomas F. Woods; Michael J. Jaro; Harold Pattom

[57] ABSTRACT

A method of modifying the surface characteristics of a substrate, particularly a polymeric material. The method involves grafting ethylenically unsaturated monomers and attaching biomolecules, such as heparin, to the surface of the substrate, such as a polymeric material, in one step using an oxidizing metal, such as ceric ions.

30 Claims, No Drawings

6,143,354

ONE-STEP METHOD FOR ATTACHMENT OF BIOMOLECULES TO SUBSTRATE SURFACES

FIELD OF THE INVENTION

This invention relates to methods of preparing materials, preferably biocompatible materials, and typically, blood compatible materials. In particular, this invention relates to a one-step method of grafting ethylenically unsaturated monomers and attaching biomolecules, such as heparin, to the surface of a substrate.

BACKGROUND OF THE INVENTION

The development of vascular grafts and medical devices that contact physiological fluids, particularly blood, is a rapidly developing area of medicine. This has been hampered, however, by the lack of suitable synthetic materials that are stable when contacted with such fluids.

Adverse reactions between materials and blood components are predominant factors limiting the use of synthetic materials that come into contact with physiological fluids. For example, catheters, vascular grafts, and the like, tend to serve as a nidus, or focus, for the formation of thrombi (blood clots). Initial contact of such materials with blood results in deposition of plasma proteins, such as albumin, fibrinogen, immunoglobulin, coagulation factors, and complement components. The adsorption of fibrinogen onto the surface of the material causes platelet adhesion, activation, and aggregation. Other cell adhesive proteins, such as fibronectin, vitronectin, and von Willebrand factor (vWF) also promote platelet adhesion. As a result, the continual use of anticoagulants in conjunction with the introduction of such materials to the body is often necessary.

Furthermore, complement activation occurs when materials are introduced into blood. Adsorption of large amounts of IgG, IgM, and C3b onto surfaces causes activation. Subsequently, complexes may be formed which contribute to undesirable immune responses, such as proteolysis, cell lysis, opsonization, anaphylaxis, and chemotaxis. As a result, these responses render such materials incompatible with the living body.

A number of approaches have been suggested to improve the biocompatibility, and even blood compatibility, of medical devices. Heparinization of polymers is one such approach. In one method, heparin is complexed with a quaternary amine prior to coating the complex onto a polymeric surface. Heparin can also be immobilized onto segmented polyurethane-urea surfaces using hydrophilic poly(ethylene oxide) spacers of different chain lengths, as disclosed in K.D. Park et al., *J. Biomed. Mater. Res.*, 22, 977–992 (1988).

Another heparinization method, which is disclosed in U.S. Pat. No. 5,229,172 (Cahalan et al.), involves initially irradiating a polymeric surface in the presence of an oxygen source and then grafting acrylamide to the irradiated surface using an acrylamide monomer and ceric ions. The grafted acrylamide surface, which can optionally be modified to include pendant functional groups such as amine and carboxyl groups, provides a suitable surface to which a biomolecule can be ionically or covalently bonded. For example, the graft can be subjected to hydrolysis in order to introduce carboxyl groups, to which spacer molecules like ethylenediamine can be coupled, using carbodiimide. To the aminated graft biomolecules such as heparin can be bound using a coupling agnet such as carbodiimide.

Thus, many of the methods of attaching biomolecules, particularly heparin, to surfaces involve multiple steps. In addition to the steps discussed above, the biomolecule may initially be modified to include reactive functional groups. For example, heparin is often oxidized by a periodate to form aldehyde functional groups.

Thus, a need exists for more efficient methods for attaching biomolecules, particularly heparin, to surfaces, particularly those that form a part of a medical device.

SUMMARY OF THE INVENTION

The present invention provides methods for attaching biomolecules, such as heparin, to substrate surfaces. Preferably, the present invention provides methods for making medical devices having biomolecules attached to (e.g., immobilized on) a substrate surface. The substrate can be made of metal or an organic polymer (i.e., a solid polymeric material).

Significantly, the methods of the present invention result in grafting to the substrate surface an ethylenically unsaturated monomer and attaching a biomolecule in one efficient step. This can result in forming a biocompatible material that includes a surface having a grafted polymer attached thereto. Preferably, the grafted polymer is a grafted hydrogel polymer. Generally, a hydrogel polymer is distinct from a solid polymeric material, of which the substrate can be made, in the amount of water contained therein. Typically, a solid polymeric material includes less than about 10 wt-% water.

Specifically, the present invention provides a method of making a medical device having a biomolecule immobilized on a substrate surface. The method includes contacting the substrate surface with a biomolecule in the presence of a source of oxidizing metal ions and an ethylenically unsaturated monomer under conditions effective to immobilize the biomolecule. Preferably, the method involves immersing the substrate in a reaction mixture that includes an aqueous solution of one or more types of biomolecules, one or more sources of oxidizing metal ions, and one or more types of ethylenically unsaturated monomers.

The present invention also provides a method of modifying the surface characteristics of a polymeric material, that may or may not form a part of a medical device. The method involves contacting the solid polymeric material with a reaction mixture that includes a biomolecule, oxidizing metal ions, and an ethylenically unsaturated monomer under conditions effective to immobilize the biomolecule. Preferably, the reaction mixture includes: a liquid carrier; a biomolecule in an amount of about 0.02 wt-% to about 1.0 wt %, based on the total weight of the reaction mixture; $Ce^{4+}$ ions at a concentration of about 0.001 M to about 0.01 M, based on the total volume of the reaction mixture; and an ethylenically unsaturated monomer in an amount of about 10 wt-% to about 50 wt-%, based on the total weight of the reaction mixture.

Similarly, the present invention provides a method of modifying the surface characteristics of a metal surface coated with a vinylsilane, that may or may not form a part of a medical device. The method involves contacting the metal surface coated with a vinylsilane with a reaction mixture that includes a biomolecule, oxidizing metal ions, and an ethylenically unsaturated monomer under conditions effective to immobilize the biomolecule.

The methods of attaching biomolecules to substrate surfaces according to the present invention can provide articles for providing sustained-release drug delivery. Thus, the present invention provides a method of delivering a biologically active agent that involves initially contacting a substrate surface with a reaction mixture comprising at least one drug, oxidizing metal ions, and an ethylenically unsaturated monomer under conditions effective to immobilize the biologically active agent. Subsequently, the method includes contacting the substrate surface having the biologically active agent attached thereto to a physiological solution under conditions effective to release the biologically active agent. The substrate surface can be made of a solid polymeric material or a metal coated with a vinylsilane.

A "medical device" may be defined as a device that has surfaces that contact tissue, blood, or other bodily fluids in the course of their operation, which fluids are subsequently used in patients. This can include, for example, extracorporeal devices for use in surgery such as blood oxygenators, blood pumps, blood sensors, tubing used to carry blood or other devices that contact blood which is then returned to the patient. This can also include endoprostheses implanted in blood contact in a human or animal body such as vascular grafts, stents, pacemaker leads, heart valves, and the like that are implanted in blood vessels or in the heart. This can also include devices for temporary intravascular use such as catheters, guide wires, and the like, which are placed into the blood vessels or the heart for purposes of monitoring or repair.

A "biomolecule" is defined as a biologically active molecule. It can include a variety of drugs (i.e., biologically active agents).

A "biocompatible" material is one that does not generally cause significant adverse reactions (e.g., toxic or antigenic responses) in the body, whether it degrades within the body, remains for extended periods of time, or is excreted whole. Ideally, a biocompatible material will not induce undesirable reactions in the body as a result of contact with bodily fluids or tissue, such as tissue death, tumor formation, allergic reaction, foreign body reaction (rejection), inflammatory reaction, or blood clotting, for example.

DETAILED DESCRIPTION OF THE INVENTION

The biocompatibility of materials used in medical devices, which include implantable materials or materials that are not necessarily implanted but that come into contact with bodily tissues or fluids (e.g., blood), can be improved by attaching (e.g., covalently), at least one type of biomolecule (e.g., heparin), using a one-step method involving oxidizing metal ions and at least one type of ethylenically unsaturated monomer, such as acrylamide. Significantly, this method does not require the use of coupling agents (i.e., activating agents), such as carbodiimide. Also, spacer molecules, such as ethylenediamine, are not required in the methods of the present invention. Using the methods of the present invention, the extent and severity of adverse reactions between the substrate and bodily fluids, particularly blood, is reduced due to the improved biocompatibility of the substrate surface.

According to the present invention, a substrate surface is contacted with one or more types of biomolecules (e.g., heparin), in the presence of one or more types of oxidizing metal ions and one or more types of ethylenically unsaturated monomers, typically in a liquid carrier (e.g., water, an organic solvent, or mixtures thereof) in which the biomolecule(s) and ethylenically unsaturated monomer(s) are sufficiently soluble. The substrate surface being treated is contacted with (e.g., immersed in or flushed with) the mixture at a sufficient temperature and for a sufficient time to complete the reaction (i.e., attach the biomolecule(s)).

The level of attachment desired, the types of reactants, the solvents used, etc., can cause the temperature and time of the reaction to vary. Preferably, the reaction time ranges from about 15 minutes to about 2 hours, and more preferably, about 30 minutes to about 90 minutes, at temperatures ranging from about 10° C. to about 50° C., and preferably, at about room temperature (i.e., about 22° C. to about 28° C.). For example, at room temperature, a polyurethane substrate can be contacted with an aqueous solution of heparin sulfate, ceric ions, and acrylamide over a period of about 45 minutes to about 75 minutes for effective heparin attachment in one step.

This "one-step" method is much more efficient than the method of U.S. Pat. No. 5,229,172 (Cahalan et al.) in that both grafting of the ethylenically unsaturated monomer (e.g., acrylamide) to the substrate surface and attachment of the biomolecule (e.g., heparin) occurs in one step. Thus, as used herein, the "one-step" method refers to polymer grafting and biomolecule attachment in one step. This "one-step" method, however, can include one or more pretreatment or post-treatment steps of the surface, if desired. For example, the surface can be cleaned, as with isopropanol or other organic solvents. Additionally, a polymer surface can be optionally irradiated with ionizing radiation, using plasma or corona discharge, for example, to activate the substrate surface toward grafting, as described in U.S. Pat. No. 5,229,172 (Cahalan et al.). It can also be optionally chemically modified prior to the combined grafting/attaching step to include pendant functional groups. Furthermore, the methods of the present invention can include subsequent washing steps, if desired.

Thus, the phrase "one-step" is used to emphasize that the primary grafting and attaching steps occur substantially simultaneously using one reaction mixture, although the overall process can include more steps, particularly polymer substrate pretreatment. This "one-step" method of grafting and attaching does not require the use of coupling agents (e.g., carbodiimide) or spacer molecules (e.g., ethylenediamine) other than the ethylenically unsaturated monomers. Thus, the biomolecules can be directly attached to the substrate through the ethylenically unsaturated monomers, which preferably form a graft polymer.

Biomolecules useful in the methods of the present invention are those that include moieties that are activated toward a substrate and/or ethylenically unsaturated monomers by oxidizing metal ions such that bonding occurs. Although not intending to be limited by theory, it is believed that the oxidizing metal ions react with the moieties to form free radicals. Such moieties can be inherent to the polymer structure or can be generated by chemical modification, for example. Exemplary such moieties include, but are not limited to, carbonyl, carboxyl, hydroxyl, amino, mercapto, urethane, ether, hydroperoxide groups, and combinations thereof.

Generally, biomolecules used according to this invention can be, for example: antibacterial and antimicrobial agents; anticoagulant and antithrombotic agents; antiplatelet agents; anti-inflammatories; enzymes; catalysts; hormones; growth factors; drugs; vitamins; antibodies; antigens; nucleic acids; dyes (which act as biological ligands); DNA and RNA; and proteins and peptides. The biomolecules can be synthetically derived or naturally occurring. These biomolecules include, for example, heparin, heparin sulfate, dermatan sulfate, prostaglandin $E_1$ (PGE1), ticlopidine, plasmin, urokinase, and TPA. Other examples are disclosed in U.S. Pat. No. 5,229,172 (Cahalan et al.). Various combinations of biomolecules can be used if desired. Heparin, and salts of heparin, such as heparin sulfate, are particularly preferred as they are believed to inhibit the coagulation of blood by interacting with antithrombin III and thrombin to inhibit the conversion of fibrinogen to fibrin. Significantly, with the methods of the present invention, heparin can be used in a wide variety of forms. For example, it may or may not be chemically modified, and/or it may or may not be fractionated by molecular weight.

The substrates that can be modified by the methods of the present invention include metals or solid polymeric materials that are substantially insoluble in body fluids and that are generally designed and constructed to be placed in or onto the body or to contact fluid of the body. The substrates preferably have the physical properties such as strength, elasticity, permeability, and flexibility required to function for the intended purpose; can be purified, fabricated, and sterilized easily; will substantially maintain their physical properties and function during the time that they remain implanted in or in contact with the body. The substrates used in the present invention may be in a wide variety of shapes or forms, such as powders, plates, strips, films, sheets, fibers, fabrics, filaments, tubing, and cast, extruded or compressed articles, and the like.

Preferred substrates include a solid organic polymeric material and may include a wide variety of natural or synthetic polymers. Polymeric materials suitable for use in the substrates are those that include moieties that are activated toward biomolecules and/or ethylenically unsaturated monomers by oxidizing metal ions such that bonding occurs. Although not intending to be limited by theory, it is believed that the oxidizing metal ions react with the moieties to form free radicals. Such moieties can be inherent to the polymer structure or can be generated by preactivation using, for example, corona treatment, ozone treatment, acid etching, chemical modification, or other methods such as those disclosed in U.S. Pat. No. 5,229,172 (Cahalan et al.). Exemplary such moieties include, but are not limited to, carbonyl, carboxyl, hydroxyl, amino, mercapto, urethane, ether, hydroperoxide groups, and combinations thereof.

Examples of suitable polymeric substrates include, but are not limited to: polyolefins including polyethylene, polypropylene, polyisobutylene, and ethylene-alpha-olefin copolymers; silicones, such as polydimethylsiloxane; acrylic polymers and copolymers, such as polyacrylate, polymethylmethacrylate (PMMA), and polyethylacrylate; vinyl halide polymers and copolymers, such as polyvinyl chloride; fluoropolymers, such as polytetrafluoroethylene, chlorotrifluoroethylene, fluorinated ethylenepropylene, polyvinylidene fluoride (PVDF), and ethylene tetrafluoroethylene copolymer (ETFE); polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; natural and synthetic rubbers, such as butadiene-styrene copolymers, polyisoprene, synthetic polyisoprene, polybutadiene, butadiene-acrylonitrile copolymers, polychloroprene rubbers, polyisobutylene rubber, ethylene-propylenediene rubber, isobutylene-isoprene copolymers, and polyurethane rubber; polyamides, such as Nylon 66 and polycaprolactam; polyesters, such as polyethylene terephthalate; alkyd resins; formaldehyde-containing resins, such as phenol-formaldehyde resins, urea-formaldehyde resins, and melamine-formaldehyde resins; polycarbonates; polyoxymethylenes; polyimides; polyethers; epoxy resins; polyurethanes; wool; cotton; silk; rayon; rayon-triacetate; cellulosics, such as cellulose acetate, cellulose butyrate, cellulose acetate butyrate, cellulose nitrate, cellulose propionate, cellulose ethers, and carboxymethyl cellulose; polyether block amides; polycarbonates; polyvinyl pyrrolidones; n-butyl cyanoacrylate; polyvinyl alcohols; acrylonitrile butadiene ethylene; styrene acrylonitrile; and the like. Substrates made using these materials can be coated or uncoated, and derivatized or underivatized, prior to being treated with one or more biomolecules. A preferred group of polymers includes those selected from the group of a polyurethane, a polyolefin, a silicone, a fluoropolymer, a polyester, a polyether, a polyamide, and blends and copolymers thereof. As used herein a copolymer includes terpolymers, tetrapolymers, etc. More preferred polymers include polyurethane or a polyether block amide.

Although solid polymeric materials are preferred, other suitable substrates include metals such as titanium/titanium alloys, TiNi (shape memory/super elastic), aluminum oxide, platinum/platinum alloys, stainless steels, MP35N, elgiloy, haynes 25, and stellite. Such metal substrate are preferably coated with a silane compound having pendant vinyl functionality. Such vinylsilanes preferably are of the formula $H_2C=CH—R—Si—X_3$, wherein R is optional and can be a short chain alkyl group, and X is a halogen, methoxy, or ethoxy group. The surface modification of a metal substrate in such a manner is further described in U.S. Pat. No. 5,607,475 (Cahalan et al.).

Oxidizing metal ions ($Ce^{+4}$, $Fe^{+3}$, $V^{+5}$, $Co^{+3}$, $Cr^{+6}$, $Fe^{+2}$, $Mg^{+3}$, and $Ni^{+2}$) are preferably introduced into the reaction mixture (which is preferably a solution) in the form of a salt. For example, among the ceric salts adapted for use in the present invention are ceric nitrate, ceric sulfate, ceric ammonium nitrate, ceric ammonium sulfate, ceric ammonium pyrophosphate, ceric iodate, ceric salts of organic acids such as ceric naphthenate and ceric linoleate, and the like. Mixtures of various salts of oxidizing metals can be used if desired.

Suitable ethylenically unsaturated monomers for use in the present invention typically include one or two carbon-—carbon double bonds. Preferably, the ethylenically unsaturated monomers include those that contain one carbon-carbon double bond (e.g., mono-vinyl monomers) or a mixture of those containing one and two carbon—carbon double bonds. Monomers containing two carbon—carbon double bonds (e.g., di-vinyl monomers) are typically capable of crosslinking and help decrease the release rate of heparin. The ethylenically unsaturated monomers can include, but are not limited to: vinyl monomers such as n-vinylpyrrolidone, styrene, and acrylonitrile; acrylates such as acrylamide, N,N-methylene diacrylamide, aminopropyl acrylate, aminoethyl acrylate, ethylacrylate, acrylic acid; and methacrylates such as polyethyleneglycol methacrylate, hydroxyethyl methacrylate, glycidyl methacrylate, butyl methacrylate, and methacrylic acid.

The methods of the present invention are typically carried out in a liquid carrier such as water, although organic solvents can be used alone or in combination with each other or with water. The liquid carrier is typically chosen such that the biomolecules and ethylenically unsaturated monomers are sufficiently soluble to result in effective attachment of the biomolecules.

The oxidizing metal ions are believed to interact with the biomolecules and the substrate surface (e.g., organic polymeric material or vinylsilane coated metal) to form free radicals, thereby resulting in grafting and attachment in one step through free radical polymerization. This grafting and attachment may involve a variety of interactions, including chemical interactions such as covalent bonding and ionic bonding, as well as physical interactions such as physical entanglement. Although the inventors do not wish to be bound by theory, it is believed that the ethylenically unsaturated monomers are grafted to the substrate to provide a matrix that provides sites for covalent and/or ionic interactions. It is also believed that this may be supplemented with physical entanglement of the biomolecules within the matrix.

The ethylenically unsaturated monomers, which may be a mixture of different monomers, are present in the reaction mixture (e.g., a solution of a biomolecule, a source of oxidizing metal ions, and an ethylenically unsaturated monomer) in an amount sufficient to provide a desired level of biomolecule attachment. Preferably, this involves an amount of at least about 10 percent by weight (wt-%), and more preferably, at least about 35 wt-%, based on the total weight of the reaction mixture. Preferably, the ethylenically unsaturated monomers are present in the reaction mixture in an amount of no more than about 50 wt-%, more preferably, no more than about 45 wt-%, and most preferably, no more than about 40 wt-%, based on the total weight of the reaction mixture. Typically, these percentages refer to the total weight of ethylenically unsaturated monomers. If crosslinkable ethylenically unsaturated monomers (e.g., those containing two carboncarbon double bonds) are used, they are preferably used in an amount of at least about 0.05 wt-%, and more preferably, at least about 0.1 wt-%. Preferably, such crosslinkable monomers are present in the reaction mixture in an amount of no more than about 5.0 wt-%, based on the total weight of the reaction mixture.

Biomolecules, which can be a mixture of different biomolecules, are present in the reaction mixture (preferably, in the form of a solution) in an amount sufficient to provide a desired level of biomolecule attachment. Preferably, this involves an amount of at least about 0.02 wt-%, and more preferably, at least about 0.05 wt-%, based on the total weight of the reaction mixture. Preferably, the biomolecules are present in the reaction mixture in an amount of no more than about 1.0 wt-%, more preferably, no more than about 0.75 wt-%, and most preferably, no more than about 0.5 wt-%, based on the total weight of the mixture.

The amount of oxidizing metal ions utilized in the methods of the present invention vary over a relatively wide range. Typically, the oxidizing metal ion concentration, preferably, the ceric ion concentration $[Ce^{+4}]$, in the reaction mixture is an amount sufficient to initiate the reaction and provide a desired level of biomolecule attachment. Preferably, the concentration of oxidizing metal ions in the reaction mixture is at least about $1 \times 10^{-6}$ molar (0.000001 M), more preferably, at least about 0.001 M, even more preferably, at least about 0.003 M, and most preferably, at least about 0.005 M, based on the total volume of the reaction mixture. The lower concentrations (e.g., 0.001 M and below) can be used if the grafting/attaching reaction is carried out in the absence of oxygen, which can be accomplished by bubbling nitrogen or argon, for example, through the reaction mixture. Preferably, $[Ce^{+4}]$ is no more than about 0.1 M, and more preferably, no more than about 0.01 M. Above about 0.01 M, it is believed that the oxidizing metal ions can cause chain termination in a free radical polymerization process, thereby reducing the level of biomolecule attachment to the substrate surface.

Because salts are typically used to introduce the oxidizing metal ions, the reaction mixture can also include one or more acids or salts that provide appropriate ion balance (i.e., charge balance). Preferably, this "charge balance reagent" is an acid and more preferably, a mixture of an acid and a salt. This reduces the amount of homopolymerization of the ethylenically unsaturated monomers. For example, nitric acid, optionally in combination with copper nitrate, can be used in a reaction mixture containing ceric ammonium nitrate. Typically, the salt or acid contains the same counterion (i.e., anion) contained in the salt of the oxidizing metal ions. The amount used depends on the amount of cerium salt used. Preferably, this charge balance reagent is present in the reaction mixture at a concentration of at least about 0.001 M, more preferably, at least about 0.06 M, and most preferably, at least about 0.1 M, based on the total volume of the reaction mixture. Preferably, this charge balance reagent is present in the reaction mixture in a concentration of no more than about 0.3 M. Preferably, a mixture of nitric acid and copper nitrate is used, wherein the nitric acid is present at a concentration of about 0.06 M to about 0.3 M, and the copper nitrate is present at a concentration of about 0.001 M to about 0.1 M.

The substrate modified according to the methods of the present invention is believed to include chains pendant from the substrate surface in which the main chain includes copolymerized ethylenically unsaturated monomers and biomolecules. The resultant modified substrate can include a wide range of levels of biomolecule attachment. Preferably, the methods of the present invention can provide loading capacities as high as 5 μg of biomolecules per square centimeter of modified surface and bioactivities as high as 0.25 International Unit (IU) thrombin (IIa) deactivated per square centimeter of modified surface. For those substrates modified with heparin, the surface is generally slippery to the touch and hydrophilic.

The modified substrates of the present invention can demonstrate release of the biomolecules over an extended period of time. For example, polyurethane modified with about 2.0 μg/cm heparin demonstrates a sustained release in a physiological solution (specifically, 0.9 wt-% NaCl solution) of about 0.03 μg/cm to about 0.07 μg/cm during a 180 minute period. Thus, the modified substrates of the present invention can be designed for sustained drug release. This is particularly controllable by the amount of crosslinker (e.g., di-vinyl monomer) included in the reaction mixture. For example, the more crosslinker, the slower heparin will release.

The materials of the present invention include a substrate and a biomolecule attached via the methods of the present invention (via ethylenically unsaturated monomers without the need for other spacer groups or coupling agents) in an amount and orientation effective to provide an improved nonthrombogenic surface relative to the substrate without the biomolecule. The contact between blood and a foreign surface initiates a complex process of thrombogenesis that involves platelet adherence, aggregation, and granular release; thrombin generation; and fibrin formation. As a consequence, there are a number of parameters that can be selected as a measure of a material's thrombogenicity. Thus, evaluation of the reactions at the blood-material interface therefore typically involves a multi-parameter (i.e., multi-assay) approach. These assays include, for example, electron microscopy for platelet adhesion, platelet spread, and thrombin-antithrombin (TAT) assay, as well as others. Any one of these assays can be sufficient to show the improvements resulting from the methods of the present invention.

The blood compatibility of the material of the present invention can be demonstrated by reduced platelet adhesion upon interaction with blood when compared to the material without the biomolecule or graft polymer attached via the methods of the present invention. By this it is meant that for a substrate to which there is a biomolecule, such as heparin, attached to a substrate surface, there is a reduction in the number of platelets attached to the substrate surface per unit area relative to the same substrate without the biomolecule attached thereto when contacted with human blood. Preferably, the substrate surface of this invention is substantially nonthrombogenic, i.e., it causes little or no platelet adhesion to occur. Herein, a substantially nonthrombogenic substrate has less than about 10%, and preferably, less than about 2%, of the surface of the substrate covered by platelets. In contrast, substrates without the biomolecule and graft polymer attached thereto, as much as 15% (and even as high as 85%) of the surface can be covered with platelets under the same conditions.

The blood compatibility of the material of the present invention can also be demonstrated by reduced thrombin-antithrombin (TAT) formation upon interaction with blood when compared to the material without the biomolecule and graft polymer attached. By this it is meant that for a substrate to which there is a biomolecule, such as heparin, attached thereto, there is a reduction in the number of thrombin-antithrombin (TAT) complexes formed relative to the same substrate without the biomolecule attached thereto when contacted with human blood. Preferably, this reduction is in an amount of at least about 90%, and more preferably, at least about 95%.

Medical devices in which the biocompatible material of the present invention can be incorporated include, but are not limited to, surgical implants, prostheses, and any artificial part or device which replaces or augments a part of a living body or comes into contact with bodily fluids, particularly blood. The substrates can be in any shape or form including tubular, sheet, rod and articles of proper shape. Various medical devices and equipment usable in accordance with the invention are known in the art. Examples of devices include catheters, suture material, tubing, and fiber membranes. Examples of catheters include central venous catheters, thoracic drain catheters, angioplasty balloon catheters. Examples of tubing include tubing used in extracorporeal circuitry, such as whole blood oxygenators. Examples of membranes include polycarbonate membranes, haemodialysis membranes, and membranes used in diagnostic or biosensor devices. Also included are devices used in diagnosis, as well as polyester yarn suture material such as polyethylene ribbon, and polypropylene hollow fiber membranes.

Further illustrations of medical devices include the following: autotransfusion devices, blood filters, blood pumps, blood temperature monitors, bone growth stimulators, breathing circuit connectors, bulldog clamps, cannulae, grafts, implantable pumps, impotence and incontinence implants, intra-occular lenses, leads, lead adapters, lead connectors, nasal buttons, orbital implants, cardiac insulation pads, cardiac jackets, clips, covers, dialators, dialyzers, disposable temperature probes, domes, drainage products, drapes, ear wicks, electrodes, embolic devices, esophageal stethoscopes, fracture fixation devices, gloves, guide wires, hemofiltration devices, hubs, intra-arterial blood gas sensors, intracardiac suction devices, intrauterine pressure devices, nasal spetal splints, nasal tampons, needles, ophthalmic devices, PAP brushes, periodontal fiber adhesives, pessary, retention cuffs, sheeting, staples, stomach ports, surgical instruments, transducer protectors, ureteral stents, vaginal contraceptives, valves, vessel loops, water and saline bubbles, achtabular cups, annuloplasty ring, aortic/coronary locators, artificial pancreas, batteries, bone cement, breast implants, cardiac materials, such as fabrics, felts, mesh, patches, cement spacers, cochlear implant, defibrillators, generators, orthopedic implants, pacemakers, patellar buttons, penile implant, pledgets, plugs, ports, prosthetic heart valves, sheeting, shunts, umbilical tape, valved conduits, and vascular access devices.

Although the examples described below involve treatment on polymeric films, it is not intended that this invention be so limited.

EXPERIMENTAL EXAMPLES

The reaction mixtures used in the methods of the present invention were prepared by combining the components in the following order: the ethylenically unsaturated monomer was added to deionized water followed by nitric acid and then mixing; the heparin was then added with mixing; the copper nitrate was then added with mixing; the solution was then degassed by bubbling nitrogen through it; and finally the ceric ammonium nitrate was added with mixing.

Example 1
Modification of PU film.

A polyurethane (PU) film (PELLETHANE, Bayer, Germany) was cleaned by soaking in isopropyl alcohol for 10 minutes. After drying at 50° C. for 30 minutes, the PU film was immersed into a deionized water solution containing 40 wt-% acrylamide, 0.75 wt-% unfractionated heparin, 0.01 M ceric ammonium nitrate, and 0.1 M nitric acid at room temperature. Nitrogen gas was bubbled through the solution for several minutes and then the reaction vessel was sealed. After about 45–75 minutes, the PU film was removed from the solution and rinsed with water for several minutes. The sample was evaluated by staining with Toluidine Blue (TB) (0.2 wt-% in deionized water) for 5 minutes at room temperature. This dye uptake analysis demonstrated the immobilization of heparin.

PU tubing was modified in a similar manner.

Example 2
Modification of PEBAX film.

Polyether block amide (PEBAX) film, obtained from Elt Atochem North America, Inc., USA) was cleaned by soaking in isopropyl alcohol for 10 minutes. After drying at 50° C. for 30 minutes, PEBAX film was immersed into a deionized water solution containing 40 wt-% acrylamide, 1.0 wt-% N,N-methylenediacrylamide, 0.05 M copper nitrate, 0.75 wt-% unfractionated heparin, 0.01 M of ammonium ceric nitrate, and 0.1 M nitric acid at room temperature. Nitrogen gas was bubbled through the solution for several minutes and then the reaction vessel was sealed. After about 45—75 minutes, the PEBAX film was removed from the solution and rinsed with water for several minutes. The sample was evaluated by staining with TB as described above, which showed heparin immobilization.

Testing

Antithrombin and thrombin were purified by well known methods (Lindhout et al., *J. Biomed. Mater. Res.*, 29, 1255–1256). The 4th international standard for heparin was obtained from the National Bureau of Standards and Control, London, UK. Chromogenic substrates S2765 and S2238 were obtained from Chromogenix, Sweden. Hepes-buffer consisted of 20 mM Hepes, 0.19 M NaCl, 1.0 mg/ml bovine serum albumin, pH 7.5. Hepes-EDTA buffer was the same as the Hepes-buffer with 20 mM EDTA.

Density of Immobilized Heparin (Heparin Digest).

A sample of modified polyurethane film having a surface area of 5 cm² were prepared according to the procedure described above. Nitrous acid solution (500 µl of 0.025 M solution) and 250 µl of water were added to the sample and the reaction was carried out for 30 minutes. Amonium sulfamate solution (250 µl of 12.5% w/v) was added to the sample and mixed with the nitrous acid solution. A sample of 800 µl of the mixture was collected to which 500 µl of MBTH (3-methyl-2-benzothiazolinone hydrazone hydrochloride, 0.25% weight/volume) was added. After 15 minutes at 50° C., 500 µl of $FeCl_3$ solution was added and the reaction was carried out for an additional 20 minutes at 50° C. After cooling down to room temperature and extracting with 2.5 ml of dichloromethane, and the light absorbency of the water layer at 660 nm was determined. Unmodified PU as a control demonstrated no heparin immobilization, whereas PU modified according to the procedure described above demonstrated immobilized heparin in an amount of 2 µg/cm².

Heparin Release.

Samples of PU tubing (5 cm length) having heparin immobilized on the surface according to the above procedure was filled with 300 µl of PLASMALYTE solution (Baxter Corp.). The solution was removed after 3 hours and assayed for heparin. The heparin activity in the buffer was measured by transferring a 20 µl sample into 75 µl antithrombin solution (533 nM). After an incubation time of 3 minutes at 37° C., 5 µl of 200 nM thrombin solution was added. Samples were removed at timed intervals and assayed for residual thrombin activity. The amount of heparin was calculated from the rate of disappearance of the thrombin activity. Standard concentrations of the heparin were used for calibration of the test. To convert the bioactivity of released heparin into the heparin concentration, the factor of 190 pg heparin/IU was employed.

Unmodified polyurethane as a control demonstrated a release of 0 µg/cm² whereas polyurethane modified according to the procedure described above demonstrated a release of 0.03–0.07 µg/cm² over a 180 minute time period.

Platelet Adhesion.

Blood was drawn from the cubital vein of healthy volunteers into 0.1 volume of 3.8% sodium citrate. Citrated platelet rich plasma (PRP) was prepared by centrifugation for 15 minutes at 250× g at room temperature.

Samples of PU tubing (ID=0.5 cm, length=10 cm) having heparin immobilized on the surface according to the above procedure was exposed to citrated platelet rich plasma (364×10⁹ platelets/l) at 37° C. for 30 minutes at a flow rate of 250 µl/minute. The non-bound platelets were removed by a wash step with Hepes buffer at the same perfusion speed. The material was then exposed to 1000 µl of 1% Triton solution to lyse the platelets. The number of platelets was determined from the LDH (lactate dehydrogenase) activity in the lysate according to the procedure of T. Lindhout et al., *J. Mater. Sci. Mater. Med.*, 6, 367 (1995).

A calibration curve was constructed from citrated platelet rich plasma diluted with 1% Triton solution. The numbers were corrected for the LDH content of the plasma. These results indicated 50–80% platelet coverage for unmodified polyurethane, whereas polyurethane modified according to the procedure described above demonstrated platelet coverage of 2–10%.

Heparin Bioactivity.

Samples of PU with a surface area of 2 cm² were put in a well plate and hydrated for 10 minutes with a 0.1 N sodium chloride solution, followed by incubation of samples for 15 minutes with Antithrombin III solution in Tris buffer (pH= 7). After rinsing, thrombin solution was added to samples in Tris buffer and the incubation was carried out for 10 minutes. The residual thrombin activity in solution was analyzed with the chromogenic substrate S2238 according to the standard procedure of T. Lindhout et al., *J. Mater. Sci. Mater. Med.*, 6, 367 (1995). This test demonstrated 0.2 IU IIa deactivated thrombin/cm².

It will be appreciated by those skilled in the art that while the invention has been described above in connection with particular embodiments and examples, the invention is not necessarily so limited and that numerous other embodiments, examples, uses, modifications and departures from the embodiments, examples and uses are intended to be encompassed by the claims attached hereto. The entire disclosure of each patent and publication cited herein is incorporated by reference, as if each were individually incorporated by reference.

What is claimed is:

1. A method of making a medical device having a biomolecule immobilized on a substrate surface of a solid polymeric material containing less than 10% water, the method comprising contacting the substrate surface with a reaction mixture comprising a biomolecule, a source of oxidizing metal ions, and an ethylenically unsaturated monomer, the contacting step occurring tinder conditions effective to immobilize the biomolecule on the substrate surface in a one-step reaction.

2. The method of claim 1, wherein the contacting step further comprises immersing the substrate in the reaction mixture, the reaction mixture comprising an aqueous solution comprising one or more biomolecules, one or more sources of oxidizing metal ions, and one or more ethylenically unsaturated monomers.

3. The method of claim 2, wherein the reaction mixture further comprises: one or more biomolecules in an amount of at least about 0.02 wt-%, based on the total weight of the reaction mixture; oxidizing metal ions at a concentration of at least about 0.001 M, based on the total volume of the reaction mixture; and one or more ethylenically unsaturated monomers in an amount of at least about 10 wt-%, based on the total weight of the reaction mixture.

4. The method of claim 3, wherein the reaction mixture further comprises: one or more biomolecules in an amount of no more than about 1.0 wt-%, based on the total weight of the reaction mixture; oxidizing metal ions at a concentration of no more than about 0.01 M, based on the total volume of the reaction mixture; and one or more ethylenically unsaturated monomers in an amount of no more than about 50 wt-% based on the total weight of the reaction mixture.

5. The method of claim 1, wherein the contacting step further comprises contacting the substrate surface with the reaction mixture in a liquid carrier at a temperature of at least about 10° C. for at least about 15 minutes.

6. The method of claim 5, wherein the liquid carrier composes water.

7. The method of claim 5, wherein the temperature is room temperature.

8. The method of claim 1, wherein the biomolecule is selected from the group consisting of an antibacterial agent, an antimicrobial agent, an anticoagulant, an antithrombotic agent, an antiplatelet agent, an anti-inflammatory, an enzyme, a catalyst, a hormone, a growth factor, a drug, a vitamin, an antibody, an antigen, a nucleic acid, a dye, a DNA, an RNA, a protein, a peptide, and mixtures thereof.

9. The method of claim 8, wherein the biomolecule is synthetically derived or naturally occurring.

10. The method of claim 8, wherein the biomolecule comprises heparin or a salt thereof.

11. The method of claim 1, wherein the substrate comprises a solid organic polymer or a metal.

12. The method of claim 11, wherein the substrate comprises a solid organic polymer and the method further includes preactivating the substrate surface prior to the contacting step, wherein the preactivating step comprises one of corona treating, ozone treating, and acid etching.

13. The method of claim 11, wherein the substrate comprises a metal surface coated with a vinylsilane.

14. The method of claim 1, wherein the substrate comprises a solid organic polymer comprising moieties selected from the group consisting of carbonyl, carboxyl, hydroxyl, amino, mercapto, urethane, ether, hydroperoxide groups, and combinations thereof.

15. The method of claim 14, wherein the substrate comprises a polymer selected from the group consisting of a polyurethane, a polyolefin, a silicone, a fluoropolymer, a polyester, a polyether, a polyamide, and blends and copolymers thereof.

16. The method of claim 15, wherein the substrate comprises a polyurethane or a polyether block amide.

17. The method of claim 1, wherein the contacting step further comprises contacting the substrate with the reaction mixture, the reaction mixture comprising oxidizing metal ions introduced into the reaction mixture in the form of a ceric salt selected from the group consisting of ceric nitrate, ceric sulfate, ceric ammonium nitrate, ceric ammonium sulfate, ceric ammonium pyrophosphate, ceric iodate, ceric salts of organic acids, and mixtures thereof.

18. The method of claim 1, wherein the ethylenically unsaturated monomer is selected from the group consisting of a mono-vinyl monomer, a di-vinyl monomer, and mixtures thereof.

19. The method of claim 18, wherein the ethylenically unsaturated monomer is selected from the group consisting of a vinyl monomer, an acrylate, a methacrylate, and mixtures thereof.

20. The method of claim 19, wherein the ethylenically unsaturated monomer is selected from the group consisting of n-vinylpyrrolidone, styrene, acrylonitrile, acrylamide, N,N-methylene diacrylamide, aminopropyl acrylate, aminoethyl acrylate, ethylacrylate, acrylic acid, polyethyleneglycol methacrylate, hydroxyethyl methacrylate, glycidyl methacrylate, butyl methacrylate, methacrylic acid, and mixtures thereof.

21. The method of claim 1, wherein the surface formed is biocompatible.

22. A method of modifying the surface characteristics of a solid polymeric material containing less than 10% water, the solid polymeric material comprising a substrate surface, the method comprising contacting the substrate surface of the solid polymeric material with a reaction mixture comprising a biomolecule, oxidizing metal ions, and an ethylenically unsaturated monomer, the contacting step occurring under conditions effective to immobilize the biomolecule on the substrate surface in a one-step process.

23. The method of claim 22, wherein the reaction mixture comprises: a liquid carrier; a biomolecule in an amount of about 0.02 wt-% to about 1.0 wt-%, based on the total weight of the reaction mixture; $Ce^{4+}$ ions at a concentration of about 0.001 M to about 0.01 M, based on the total volume of the reaction mixture; and an ethylenically unsaturated monomer in an amount of about 10 wt-% to about 50 wt-%, based on the total weight of the reaction mixture.

24. The method of claim 23, wherein the contacting step comprises contacting the substrate surface with the reaction mixture at a temperature of at least about 10° C. for at least about 15 minutes.

25. The method of claim 24, wherein the temperature is room temperature.

26. The method of claim 22, wherein the biomolecule is heparin or a salt thereof and the ethylenically unsaturated monomer is acrylamide.

27. A method of modifying the surface characteristics of a metal surface coated with a vinylsilane, the method comprising contacting the metal surface coated with a vinylsilane with a reaction mixture comprising a biomolecule, oxidizing metal ions, and an ethylenically unsaturated monomer, the contacting step occurring under conditions effective to immobilize the biomolecule on the surface in a one-step process.

28. A method of delivering a biologically active agent, the method comprising contacting a substrate surface of a solid polymeric material containing less than 10% water with a reaction mixture comprising the biologically active agent, oxidizing metal ions, and an ethylenically unsaturated monomer under conditions effective to immobilize the biologically active agent on the substrate surface in a one-step reaction process; and contacting the substrate surface having the biologically active agent attached thereto to a physiological solution under conditions effective to release the biologically active agent.

29. A modified polymeric material preparable by the method of claim 22.

30. A medical device preparable by the method of claim 1.

* * * * *

UNITED STATES PATENT AND TRADEMARK OFFICE
CERTIFICATE OF CORRECTION

PATENT NO.  : 6,143,354
DATED       : November 7, 2000
INVENTOR(S) : Koulik et al.

It is certified that error appears in the above-identified patent and that said Letters Patent is hereby corrected as shown below:

Column 12,
Line 25, change "step occurring tinder" to -- step occurring under --.
Line 56, change "carrier composes water" to -- carrier comprises water --.

Signed and Sealed this

Eighteenth Day of March, 2003

JAMES E. ROGAN
*Director of the United States Patent and Trademark Office*